US006348215B1

(12) United States Patent
Straubinger et al.

(10) Patent No.: US 6,348,215 B1
(45) Date of Patent: Feb. 19, 2002

(54) STABILIZATION OF TAXANE-CONTAINING DISPERSED SYSTEMS

(75) Inventors: Robert M. Straubinger, Amherst; Sathyamangalam V. Balasubramanian, Buffalo, both of NY (US)

(73) Assignee: The Research Foundation of State University of New York, Amherst, NY (US)

( * ) Notice: Subject to any disclaimer, the term of this patent is extended or adjusted under 35 U.S.C. 154(b) by 0 days.

(21) Appl. No.: 09/684,115

(22) Filed: Oct. 6, 2000

Related U.S. Application Data (60) Provisional application No. 60/157,988, filed on Oct. 6, 1999.

(51) Int. Cl.[7] .................. A61K 9/127; C07D 305/14
(52) U.S. Cl. .................. 424/450; 549/510; 549/511
(58) Field of Search ................. 549/510, 511; 424/450

(56) References Cited

U.S. PATENT DOCUMENTS

| | | | |
|---|---|---|---|
| 4,687,661 A | 8/1987 | Kikuchi et al. | 424/38 |
| 5,151,272 A | 9/1992 | Engstron et al. | 424/450 |
| 5,415,869 A | 5/1995 | Straubinger et al. | 424/450 |
| 5,560,933 A | 10/1996 | Soon-Shiong et al. | 424/489 |

OTHER PUBLICATIONS

Sharma et al., "Paclitaxel–liposomes for intracaviary therapy of intraperitoneal P388 leukemia," Cancer Letters, 107: 265–72(1996).

Sharma et al., "Antitumor Efficacy of Taxane Liposomes on a Human Ovarian Tumor Xenograft in Nude Athymic Mice," J. Pharmaceutical Sciences, 84(12): 1400–404(1995).

Sharma et al., "Antitumor Effect of Taxol–containing Liposomes in a Taxol–resistant Murine Tumor Model," Cancer Research, 53: 5877–881(1993).

Balasubramanian et al., Solvent–and Concentration–Dependent Molecular Interactions of Taxol (Paclitaxel), J. Pharmaceutical Seciences, 83(10): 1470–476(1994).

Sharma et al., "Pharmaceutical and Physical Properties of Paclitaxel (Taxol) Complexes with Cyclodextrins," J. Pharmaceutical Sciences, 84(10): 1223–230(1995).

Balasubramanian et al., "Taxol–Lipid Interactions: Taxol–Dependent Effects on the Physical Properties of Model Membranes," Biochemistry, 33(30): 8941–947(1994).

Sharma et al., "Novel Taxol Formulations: Preparation and Characterization of Taxol–Containing Liposomes," Pharmaceutical Research, 11(6): 889–96(1994).

*Primary Examiner*—Ba K. Trinh
(74) *Attorney, Agent, or Firm*—Braman & Rogalskyj LLP (57) ABSTRACT

The invention provides a method of stabilizing a taxane in a dispersed system, which method comprises exposing the taxane to a molecule which improves physical stability of the taxane in the dispersed system. By improving physical stability of the taxane in the dispersed system, higher taxane content can be achieved. The invention thus further provides a stable taxane-containing liposome preparation comprising a liposome containing one or more taxanes present in the liposome in an amount of less than 20 mol % total taxane to liposome, wherein the liposome is suspended in a glycerol:water composition having at least 30% glycerol.

20 Claims, 4 Drawing Sheets

STABILIZATION OF TAXANE-CONTAINING DISPERSED SYSTEMS

This application claims priority of U.S. Provisional Patent Application No. 60/157,988, filed Oct. 6, 1999.

FIELD OF THE INVENTION

The subject invention is directed generally to dispersed systems and more particularly to a method of stabilizing a taxane in a dispersed system, and to a stable taxane-containing liposome preparation.

BACKGROUND OF THE INVENTION

Throughout this application various publications are referenced, many in parenthesis. Full citations for each of these publications are provided at the end of the Detailed Description. The disclosures of each of these publications in their entireties are hereby incorporated by reference in this application.

Figure 1:
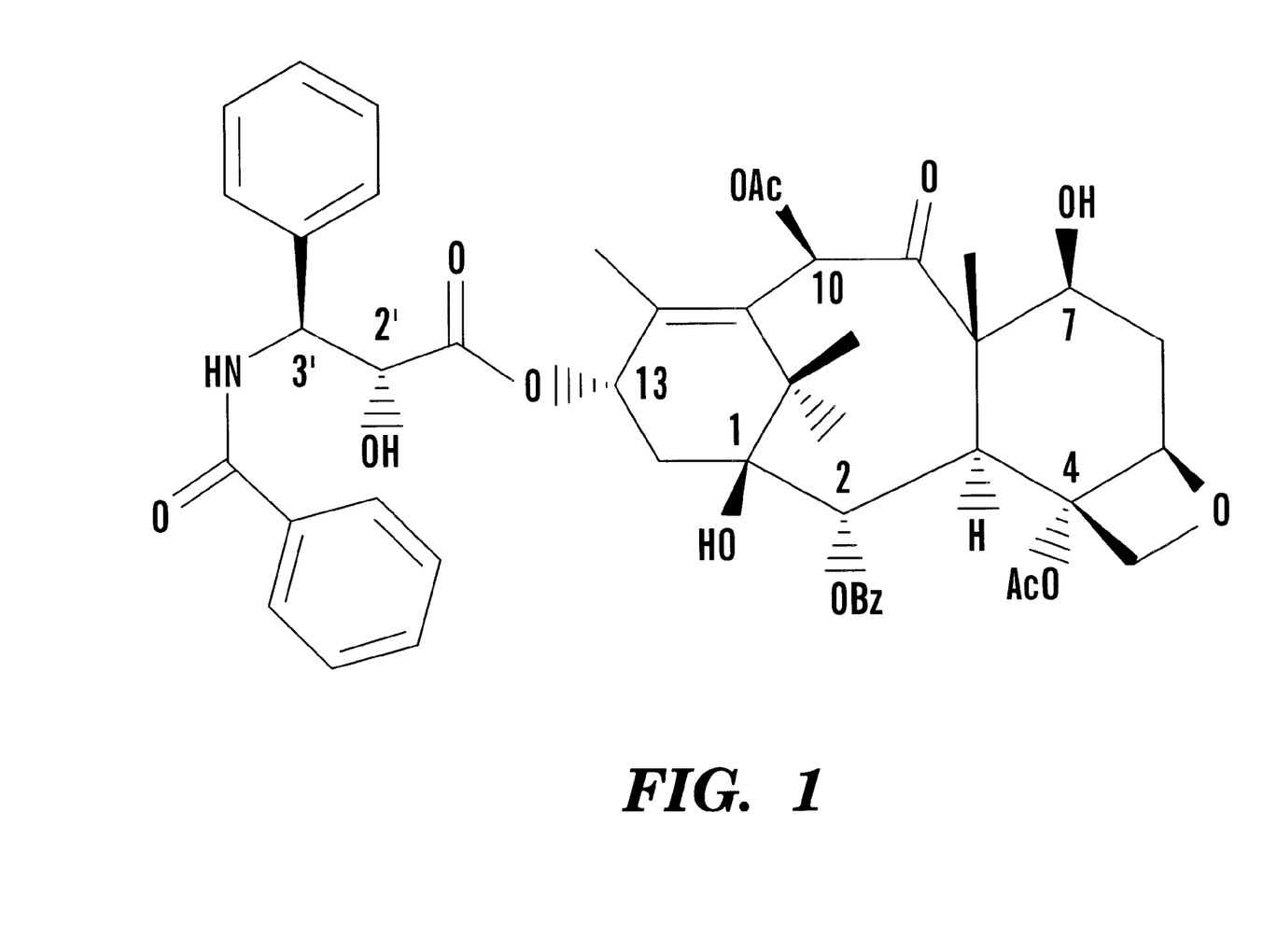
FIG. 1 shows the structure of paclitaxel, showing numbering of groups.

Paclitaxel (taxol, FIG. 1) is a diterpenoid natural product that is undergoing intensive evaluation as an anticancer agent (Wani et al. 1971; Donehower et al. 1987; Grem et al. 1987; Rowinsky et al. 1990). The clinical development of all taxanes, including the prototype paclitaxel, has been hampered by poor aqueous solubility (Suffness 1993; Straubinger 1995), which necessitates administration of the drug in a vehicle such as Cremophor EL mixed with ethanol. Unfortunately, the formulation vehicle causes a variety of adverse reactions, including anaphylactoid hypersensitivity reactions (Donehower et al. 1987; Lorenz et al. 1977). Newer semisynthetic taxanes in clinical use (eg. docetaxel (Taxotere)) have greater water solubility, but a potentially toxic solubilizer (polysorbate 80) nonetheless is required for administration (Bissery et al. 1991; Tomiak et al. 1992).

Previously, phospholipid-based liposome formulations for paclitaxel, Taxotere, and other active taxanes have been developed (Straubinger et al. 1993; Straubinger et al. 1994; Sharma et al. 1993; Sharma and Straubinger 1994; A. Sharma et al. 1995a), and the physical properties of these and other taxane formulations have been studied (Sharma and Straubinger 1994; U.S. Sharma et al. 1995; Balasubramanian and Straubinger 1994; Balasubramanian et al. 1994). The main utility of these formulations is the elimination of toxicity related to the Cremophor EL excipient, and a reduction in the toxicity of the taxane itself, as demonstrated in several animal tumor models (Sharma et al. 1993; A. Sharma et al. 1995; Sharma et al. 1996). This observation holds for several taxanes in addition to paclitaxel (A. Sharma et al. 1995). In some cases, the antitumor potency of the drug appears to be slightly greater for the liposome-based formulations (Sharma et al. 1993).

These formulations consist of phospholipids and other additives, in addition to the taxane, and may be stored in a dried state. Upon addition of an aqueous phase to the mixture, particles form spontaneously and may take the form of liposomes (Straubinger et al. 1993). Liposomes are closed, vesicular structures consisting of a limiting bilayer membrane surrounding an aqueous core. A preferred formulation composition (Sharma and Straubinger 1994) contains a neutral (zwitterionic) phospholipid such as lecithin (phosphatidylcholine, 80–90% by mole ratio), along with a negatively charged phospholipid such as phosphatidylglycerol (10–20%). The latter prevents aggregation of the particles through electrostatic repulsion. The most stable taxane content is in the range of 3–4 mole % (relative to total phospholipid content); such liposomes may be physically and chemically stable for 2 months after hydration. Under most conditions, paclitaxel formulations containing higher (eg. 8 mole %) drug concentrations are very unstable and may precipitate within minutes of preparation (Sharma and Straubinger 1994).

The greatest concern over these formulations has been the relatively low taxane content of acceptably stable formulations (3–5 mole %), which necessitates the administration of a large amount of phospholipid (5–10 gm) to patients in order to give the anticipated dose of drug. Although humans frequently are given large amounts of lipids intravenously for Total Parenteral Nutrition (TPN), a major developmental aim has been to produce taxane liposomes having a higher taxane content.

SUMMARY OF THE INVENTION

The subject invention addresses this need by providing a method of stabilizing a taxane in a dispersed system, which method comprises exposing the taxane to a molecule which improves physical stability of the taxane in the dispersed system. By improving physical stability of the taxane in the dispersed system, higher taxane content can be achieved. The invention thus further provides a stable taxane-containing liposome preparation comprising a liposome containing one or more taxanes present in the liposome in an amount of less than 20 mol % total taxane to liposome (preferably 9–20 mol %), wherein the liposome is suspended in a glycerol:water composition having at least 30% glycerol.

BRIEF DESCRIPTION OF THE DRAWINGS

These and other features and advantages of this invention will be evident from the following detailed description of preferred embodiments when read in conjunction with the accompanying drawings in which.

DETAILED DESCRIPTION OF THE INVENTION

The subject invention provides a method of stabilizing a taxane in a dispersed system, which method comprises exposing the taxane to a molecule which improves physical stability of the taxane in the dispersed system. According to one embodiment of the method of the subject invention, the taxane can be exposed to the molecule by forming a taxane-containing dispersed system, and then exposing the taxane-containing dispersed system to the molecule. In this embodiment, for example, a paclitaxel-containing liposome may be formed which is then suspended in a glycerol:water composition. By suspending the paclitaxel-containing liposome in the glycerol:water composition, the glycerol acts as the molecule which improves physical stability of the paclitaxel in the liposome.

In an alternative embodiment of the method of the subject invention, the taxane can be exposed to the molecule, and then the resulting taxane can be incorporated into a dispersed system. In this embodiment, for example, a paclitaxel molecule can be exposed to a molecule such as $CH_3$ which will block hydroxyl groups on the paclitaxel molecule. The blockage of the hydroxyl groups prevents the "stacking" of the paclitaxel molecule with other paclitaxel molecules. This "blocked" paclitaxel molecule is then incorporated into a dispersed system, such as a liposome, and solubility of the "blocked" paclitaxel in the liposome is much improved over solubility of the "unblocked" paclitaxel in the liposome.

"Taxanes", as used herein, refers to the class of antineoplastic agents having a mechanism of microtubule action and having a structure which includes the unusual taxane ring system (see FIG. 1) and a stereospecific side chain that is required for cytostatic activity. Paclitaxel (also known as taxol)(Wani et al. 1971), the first clinically used taxane, is a naturally occurring taxane present in low abundance (0.02% by weight) in the bark of the slow-growing Western Yew, *Taxus brevifolia,* and was first obtained by a process that kills the trees. As a result, the limited supply of paclitaxel hindered widespread clinical trials. Therefore, major efforts were directed toward the development of alternative sources of paclitaxel, as well as the synthesis of active analogs from more abundant precursors. Paclitaxel can now be produced by semisynthesis from 10-deacetylbaccatin III (10-DAB III), a taxane found in yew needles, a renewable resource. Docetaxel, an active analog also in clinical trial, is synthesized from 10-DAB III (U.S. Pat. No. 4,814,470, issued Mar. 21, 1989 to Colin et al.). A taxane designated SB-T-1011 has been synthesized from 14β-hydroxy-10-DAB III, also obtained from yew needles (Ojima et al. 1994).

Paclitaxel has a structure consisting of the unusual taxane ring system (FIG. 1), along with a stereospecific side chain that is required for cytostatic activity (Wani et al. 1971). The side chain contains two aromatic rings connected by an amide (peptide-like) bond (FIG. 1), but the existence of other active analogs such as taxotere (Gueritte-Voegelein et al. 1990; Gueritte-Voegelein et al. 1991) demonstrates that certain structural modifications to the basic paclitaxel side chain motif can be tolerated. Studies of paclitaxel and synthetic analogs have led to a model in which a conformational "hydrophobic collapse" is hypothesized to accompany the transfer of paclitaxel from organic to aqueous media (Vander Velde et al. 1993).

As so defined and as used herein, taxanes include, for example, paclitaxel, 7-epitaxol, 7-acetyl taxol, 10-desacetyl-taxol, 10-desacetyl-7-epitaxol, 7-xylosyltaxol, 10-desacetyl-7-glutaryltaxol, 7-N,N-dimethylglycyltaxol, 7-L-alanyltaxol, taxotere, SB-T-1011, and mixtures thereof.

As also used herein, a "dispersed system" refers to a system consisting of an insoluble or immiscible substance dispersed throughout a continuous medium. Suitable dispersed systems for use in the subject invention include, for example, liposomes, micelles, and emulsions. A liposome, as used herein, refers to a closed vesicle of lipid bilayer or lipid monolayer. The interior of the liposome may be used to encapsulate exogenous materials or drugs for ultimate delivery into cells by fusion with the cell. A micelle, as used herein, refers to a unit of structure composed of an aggregate or oriented arrangement of molecules (for example, an aggregate formed by amphipathic molecules in water such that their polar ends are in contact with water and their nonpolar portions are in the interior of the aggregate is a micelle). An emulsion, as used herein, refers to a product consisting of minute globules of one liquid dispersed throughout the body of a second liquid. The portion that exists as globules is known as the internal, dispersed, or discontinuous phase; the other liquid is the external or continuous phase or the dispersion medium.

Figure 2:
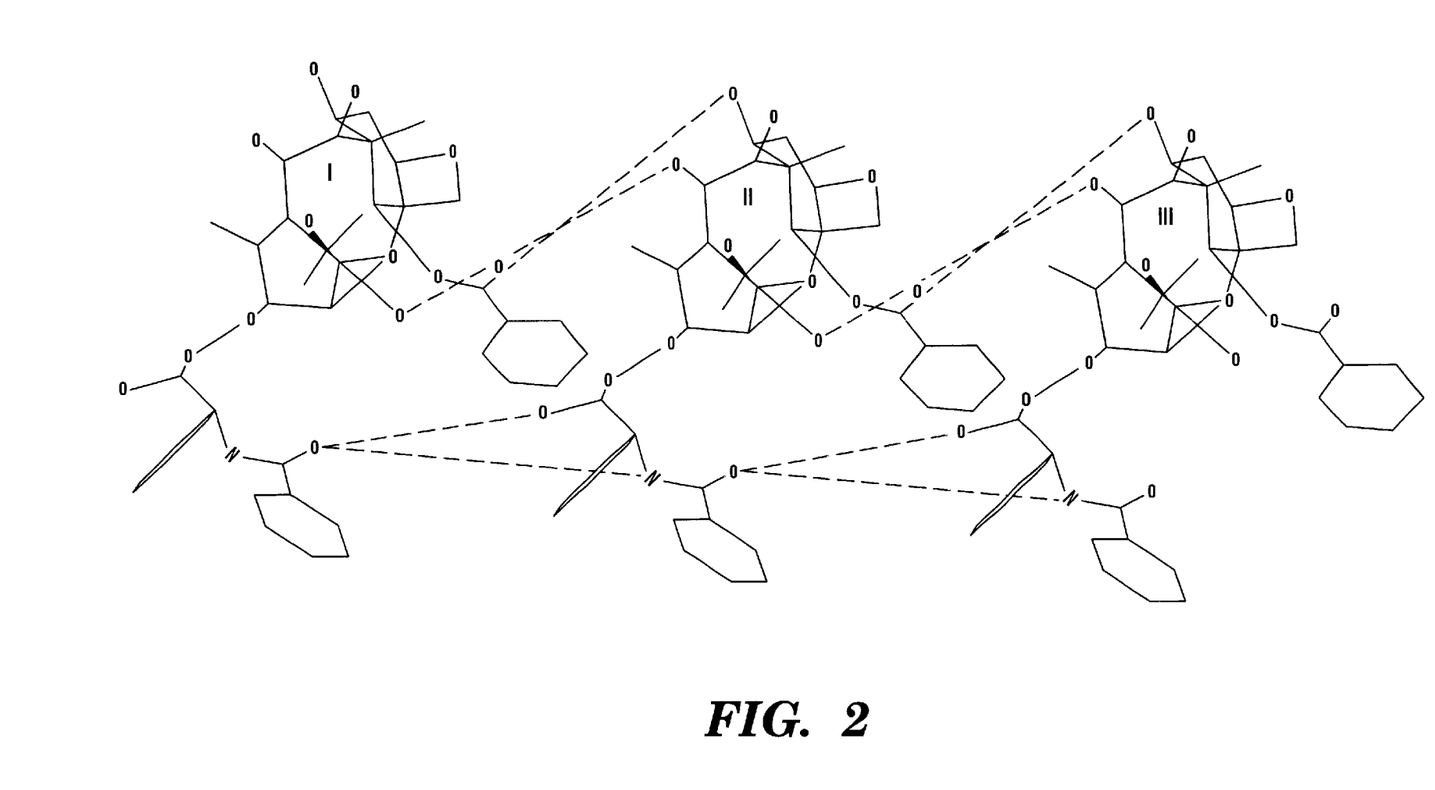
FIG. 2 shows the conformation of self-assembled (aggregated) paclitaxel in a hydrophobic environment. Conformation of each monomer is identical; monomer II is bound to both monomer I and III by hydrogen bonds.

As also used herein, a molecule which improves physical stability of a taxane in a dispersed system is a molecule which allows higher taxane content in the dispersed system without precipitation of the taxane. Precipitation of the taxane in the dispersed system is readily identified and screened for by use of optical microscopy, nuclear magnetic resonance (NMR), and circular dichroism (CD). Optical microscopy can be used to visualize precipitates in the dispersed system. For example, Differential Interference Contrast Microscopy can be used to detect aggregation of liposomes or crystallization of taxane (see Sharma and Straubinger 1994). NMR and CD studies will indicate molecules which improve solubility by decreasing stacking of taxane molecules (see Balasubramanian et al. 1994). Stacking of taxane molecules refers to the concentration-dependent aggregation of taxane molecules into stacks that are stabilized by the effects of four hydrogen-bonded functional groups (see FIG. 2). The hydrogen-bonding groups can coordinate simultaneous interactions between molecules on both of the major faces of the taxane molecules and thus propagate aggregation into higher ordered stacks (see Balasubramanian et al. 1994 for a more detailed discussion of the stacking concept).

"Stacked" taxane molecules produce a characteristic NMR pattern. The addition of a molecule which decreases stacking of taxane molecules (thereby improving solubility) to a taxane preparation will cause a loss of cross beams in the NMR pattern for the taxane preparation. "Stacked" taxane molecules also produce a characteristic CD pattern which is flat when the taxane is precipitated. The addition of a molecule which decreases stacking of taxane molecules (thereby improving solubility) to a taxane preparation will cause a deep (negative) band at about 290–295 nm and a high (positive) band at about 230 nm. A discussion of the use of NMR and CD studies to assess stacking of a taxane, and therefore solubility of the taxane, is provided in Balasubramanian et al. 1994. These three techniques, optical microscopy, NMR, and CD can therefore be used to readily screen for molecules which improve the physical stability of a taxane in a dispersed system.

Improved physical stability, as indicated, primarily refers to reduced propensity of the taxane to precipitate in the dispersed system. Improved physical stability can be obtained by improving solubility of the taxane in the dispersed system. The molecules which improve physical stability may do so by decreasing aggregation of the taxane, which includes decreasing stacking and decreasing dimerization of the taxane, for example.

Suitable molecules for use in the subject invention include, in a presently preferred embodiment, molecules which improve physical stability by decreasing stacking of the taxane. Such molecules include glycerol (presently preferred), alcohols (such as propylene glycol, polyethylene glycol, and ethanol), and dimethyl sulfoxide. When the taxane is exposed to the molecule and then a taxane-containing dispersed system is formed, suitable molecules include $CH_3$, acetic acid, and acetic anhydride.

In a presently preferred embodiment, the dispersed system is a liposome and the molecule is glycerol. In this embodiment, the preferred taxane is paclitaxel.

The invention further provides a stabilized taxane-containing dispersed system produced by the method of the subject invention.

As used herein, "taxoll" and "Paclitaxel" are used synonymously, while Taxol® denotes the paclitaxel formulation of Bristol-Myers Squibb Inc., which contains ethanol and Cremophor EL.

In a presently preferred embodiment, the invention provides a method of stabilizing paclitaxel liposomes which involves the use of glycerol as the stabilizing agent. The process of taxane precipitation and liposome destabilization has been studied intensively. The unique taxane molecular structure allows self-assembly or "stacking" (Balasubramanian et al. 1994)—with the face of one molecule adhered to the back of the next (FIG. 2)—which can propagate and thereby cause the initiation (nucleation) of crystallization. This process not only reduces the apparent taxane solubility, but also underlies the instability of liposomes having high taxane content (Balasubramanian and Straubinger 1994).

The addition of glycerol, as described herein, interrupts this "stacking" process, and thereby interferes with paclitaxel crystallization and precipitation. Furthermore, in the liposomal formulations disclosed herein, the hydrophobic paclitaxel molecule lies buried in the hydrophobic, hydrocarbon-rich domain of the membrane, just below the water-phospholipid interface. Because of its somewhat hydrophobic nature, glycerol can penetrate to the hydrocarbon-water interface, and interact with drug molecules that are located in the liposome membrane. This interaction inhibits the events that lead to destabilization of taxane liposomes.

The main significance of this invention is that stable liposomes of up to about 20% (mole drug/mole lipid), including 9–20% and 10–15%, may be prepared under conditions anticipated for use. This represents a major advancement which should enhance the likelihood of progress of the formulations to the clinic.

Others have described taxane formulations, including liposome-based formulations and emulsions. The method of stabilization by glycerol, as described herein, can also enhance stability of those formulations. Glycerol can also be employed to stabilize other taxane-containing formulations, eg. eliminating or reducing the Cremophor EL in the clinical Taxol® formulation, or the Polysorbate in the clinical Taxotere formulation, in accordance with the method of the subject invention.

Experimental evidence supporting the claim of glycerol stabilization of liposomal taxane formulations is provided below. The primary data is derived from Circular Dichroism Spectropolarimetry, using an assay that detects the stability and conformational state of paclitaxel in formulations (U.S. Sharma et al. 1995; Balasubramanian and Straubinger 1994; Balasubramanian et al. 1994).

The invention further provides a stable taxane-containing liposome preparation comprising a liposome containing one or more taxanes present in the liposome in an amount of less than 20 mol % (preferably 9–20 mol % or 10–15 mol %) total taxane to liposome, wherein the liposome is suspended in a glycerol:water composition having at least 30% glycerol.

EXAMPLE I
Preparation of Taxane-containing Lipid Vesicles

Paclitaxel was obtained from the National Cancer Institute or as a gift from TPL Phytogen Inc. (Vancouver, BC). Phospholipids were obtained from Avanti Polar Lipids (Alabaster, Ala.).

The appropriate amount of paclitaxel and the lipid (75:25 mole:mole egg PC:soybean PG) was dissolved in chloroform and the solvent was dried under reduced pressure using a rotary evaporator. The dried film was resuspended in 1 mL of a solvent system containing various ratios of glycerol:water. The drug/lipid phase thus formed (most probably in the physical form of liposomes) was examined for stability using circular dichroism (CD) and optical microscopy (U.S. Sharma et al. 1995; Balasubramanian and Straubinger 1994; Balasubramanian et al. 1994). Stability after dilution in saline was also examined using CD and optical microscopy. U.S. Pat. No. 5,415,869, issued May 16, 1995, describes the preparation of taxane-containing liposomes in detail. The entire contents of U.S. Pat. No. 5,415,869 are incorporated herein by reference.

The CD experiments were performed on a JASCO 500 instrument calibrated with d10 Camphor sulfonic acid. The path length of the quartz cuvette used was 1 mm. Spectra were acquired in the range of 220 to 350 nm, with sensitivity settings in the range of 1 or 2 m°/cm.

Optical microscopy experiments were performed using a Zeiss Axiovert microscope equipped with Differential Interference Contrast optics.

EXAMPLE II
Stability of Taxane-containing Lipid Vesicles

In order to determine the stability of the paclitaxel-containing phase ("liposomes") formed in various lecithin:glycerol:water systems, CD experiments were carried out (FIGS. 3 and 4), and the samples were analyzed by optical microscopy in parallel (Table 1). The methods provide both qualitative and quantitative information on the stability of paclitaxel formulations.

Figure 3:
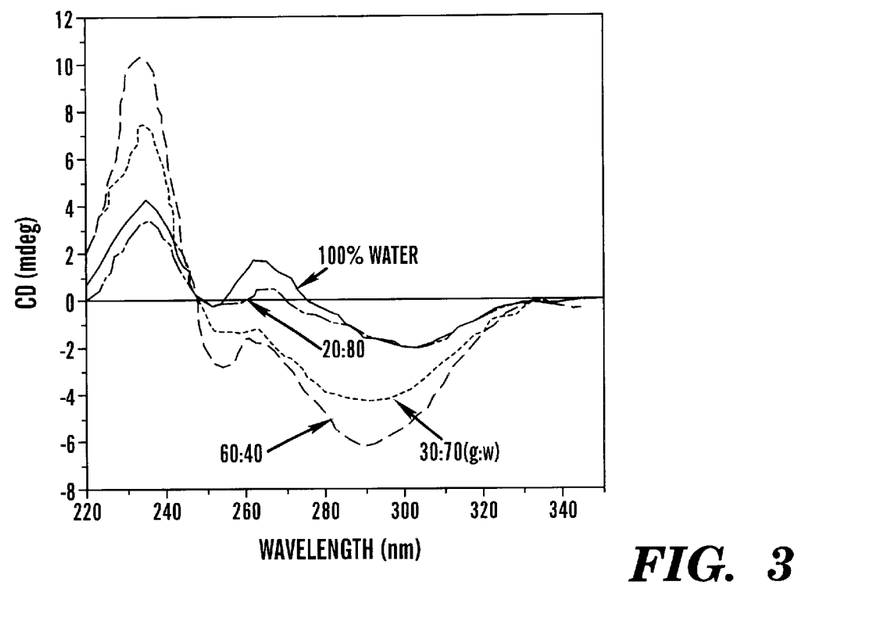
FIG. 3 shows CD spectra of paclitaxel:lipid mixtures containing 20 mole % drug and consisting of 75:25 mole:mole egg PC:soybean PG. The dry drug:lipid mixture was suspended in the glycerol/water mixtures of the compositions indicated. The spectra were acquired over the range 350 nm to 220 nm. The sensitivity was 1 m°/cm, and 1 mm cuvettes were used. [paclitaxel]=0.1 mM; [lipid]=0.5 mM.
Figure 4:
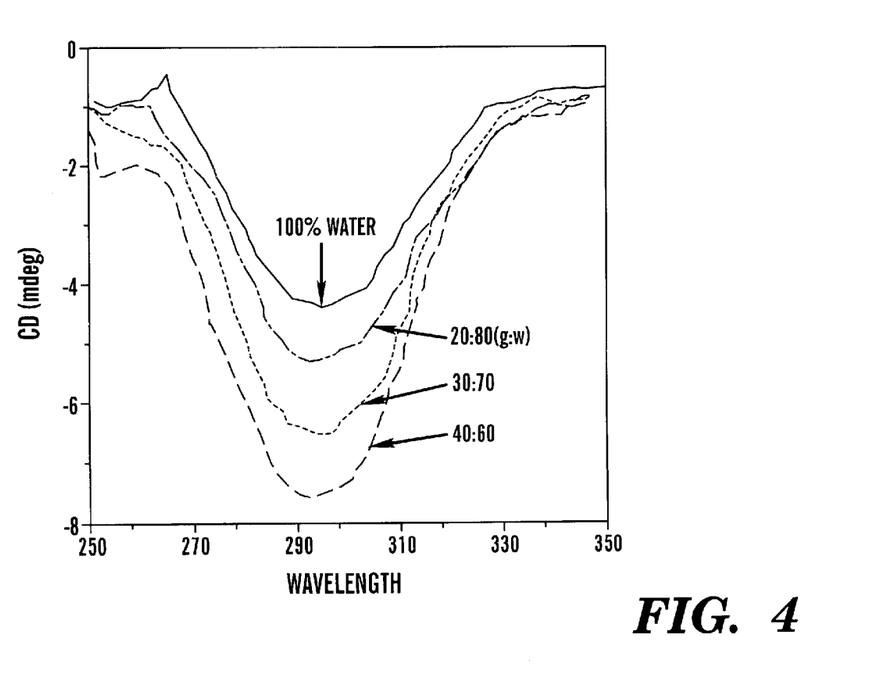
FIG. 4 shows CD spectra for paclitaxel:lipid mixtures containing 8 mole % drug which were suspended in various glycerol/water mixtures. CD spectra were acquired over the range 350 nm to 220 nm. The sensitivity was 1 m°/cm and 1 mm cuvettes were used. [paclitaxel]=0.1 mM; [lipid]=1.2 mM.

FIG. 3 shows CD spectra of paclitaxel in liposomes containing 20 mole % drug (with respect to total phospholipid) and suspended in various glycerol:water mixtures. At higher glycerol concentrations (eg. 30:70 vol:vol glycerol:water and greater), a symmetric negative band around 295 nm is observed, along with a small negative band at 250 nm, and a positive band at 232 nm. The negative band around 295 nm is due to the n—pi* transition of aromatic groups in the paclitaxel side chain and the main taxane ring system. The positive band is due to the n—pi* transition of the olefinic group, along with contributions from C=O on the C13 side chain and on the main taxane ring.

The spectra of paclitaxel:lipid mixtures suspended in 100% water, 10:90 glycerol:water (not shown), and 20:80 glycerol:water differ in several respects (FIG. 3) from spectra taken in higher glycerol concentrations. The intensity and shape of the negative band around 295 nm indicates the solubility and the physical aggregation state of paclitaxel. This nearly symmetric band displays an asymmetric exciton split band at 303 nm under conditions in which the drug undergoes self assembly (aggregation) followed by precipitation (ie. in higher aqueous content).

The CD spectrum is an averaged representation of the various drug conformations simultaneously present in the sample. In the case of liposomal paclitaxel formulations, the CD spectrum may include contributions from the stable, soluble form of drug embedded in the membrane bilayer, as well as the self-assembled, precipitated form in the water phase. This spectral property has been used to evaluate the stability of liposomal formulations.

A symmetric negative band represents the stable paclitaxel formulation, and a lower intensity, as well as exciton split bands, correspond to precipitated paclitaxel. Thus the data shows that the formulations suspended in higher glycerol concentrations ($\geq 30\%$ or greater) are stable under conditions in which samples suspended in 100% water or lower glycerol ($\leq 30\%$) are physically unstable.

Figure 5:
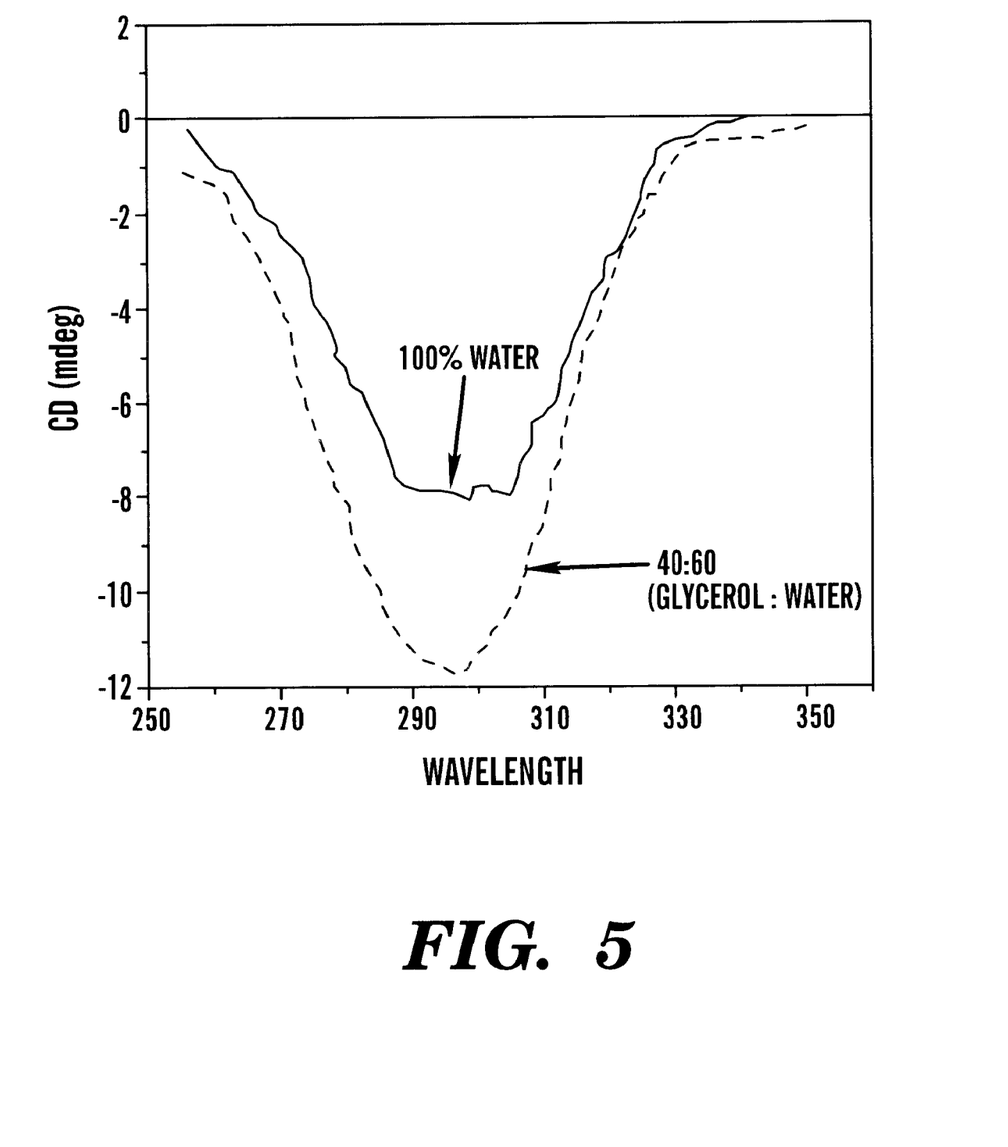
FIG. 5 shows CD spectra for paclitaxel:lipid mixtures containing 10 mole % drug which were suspended in various glycerol/water mixtures. The solution was further diluted 10-fold using saline. CD spectra were acquired over the range 350 nm to 250 nm. The sensitivity was 2 m°/cm, and 1 mm cuvettes were used. [paclitaxel]=5 mM; [lipid]=50 mM.

Similar conclusions regarding stability were made by observing formulations using optical microscopy (Table 1). Visual inspection of samples for the presence of precipitates suggested time-dependent effects; the samples suspended in higher glycerol concentrations ($\geq 40\%$) precipitated at a slower rate when compared to the samples suspended in lower glycerol concentrations. Samples containing high glycerol content remained physically stable for 10 days following solution preparation. The experiments were also performed with lower paclitaxel content (eg. 8 mole % paclitaxel) and similar stability profiles were observed (FIG. 5).

The effect of glycerol on paclitaxel formulation physical stability was examined further using preparations containing 10% paclitaxel (with respect to phospholipid). The drug/lipid mixture was suspended at various glycerol:water ratios and the stability of the solution was monitored by CD and optical microscopy. No precipitates or crystalline structures were observed 0.5–1 hr after sample preparation (Table 2). However, 2 hr after sample preparation, needle-like structures (corresponding to precipitated paclitaxel) were observed in samples having lower glycerol concentration (10–20%), whereas samples suspended in higher glycerol (eg. 70%) were stable.

Stability upon dilution was investigated for samples stabilized by glycerol. Samples containing 10 mole % paclitaxel (with respect to phospholipid) were hydrated at various glycerol:water ratios, and diluted 10-fold in saline. Stability of the diluted samples was monitored by CD spectroscopy. The intensity and the shape of the negative band around 295 nm was utilized as a marker of the precipitation. Sample suspended in 100% water showed precipitation upon dilution (FIG. 5), whereas samples suspended in $\geq 40\%$ glycerol were stable. Optical microscopy studies supported the CD data; 2 hr after dilution, samples originally suspended in $\geq 20\%$ glycerol were substantially free of crystalline paclitaxel.

Although preferred embodiments have been depicted and described in detail herein, it will be apparent to those skilled in the relevant art that various modifications, additions, substitutions and the like can be made without departing from the spirit of the invention and these are therefore considered to be within the scope of the invention as defined in the claims which follow.

TABLE 1

| Paclitaxel:lipid ratio | 8 mole % | | 20 mole % | |
|---|---|---|---|---|
| Glycerol/water ratio | 0.5 hr | 6 hr | 0.5 hr | 6 hr |
| 0:100 (100% water) | unstable | unstable | unstable | unstable |
| 10:90 | stable | unstable | unstable | unstable |
| 20:80 | stable | unstable | unstable | unstable |
| 30:70 | stable | unstable | stable | unstable |
| 40:60 | stable | stable | stable | unstable |
| 50:50 | stable | stable | stable | unstable |
| 60:40 | stable | stable | stable | stable |
| 70:30 | stable | stable | stable | stable |
| 80:20 | stable | stable | stable | stable |
| 90:10 | stable | stable | stable | stable |
| 100:0 (100% glycerol) | stable | stable | stable | stable |

Optical microscopy observations of paclitaxel:lipid mixtures containing 8 or 20 mole % drug. Samples were evaluated for the presence of needle-like drug crystals or visible precipitates immediately or 6 hr after hydration in the indicated glycerol:water mixtures. Samples containing visible precipitate were considered as unstable.

TABLE 2

| Glycerol/water ratio | undiluted | | 10-fold diluted | |
|---|---|---|---|---|
| | 0.5 hr | 2 hr | 0.5 hr | 2 hr |
| 0:100 (100% water) | stable | unstable | unstable | unstable |
| 20:80 | stable | unstable | stable | stable |
| 40:60 | stable | stable | stable | stable |
| 100:0 (100% glycerol) | stable | stable | stable | stable |

Stability upon dilution. Optical microscopy observations of paclitaxel:lipid mixtures containing 10 mole % drug. The dry lipid mixture was hydrated in the glycerol:water mixture indicated, and then some samples were diluted 10-fold with saline. The appearance of needle-like crystals or precipitates was considered as unstable.

REFERENCES

J. D. Adams, et al., J Natl Cancer Inst Monographs 15:141–147 (1993).
S. V. Balasubramanian and R. M. Straubinger, Biochemistry 33:8941–8947 (1994).
S. V. Balasubramanian, et al., J Pharm Sci 83:1470–1476 (1994).
M. Bissery, et al., Cancer Res 51:4845–4852 (1991).
R. C. Donehower, et al., Cancer Treat Rep 71:1171–1177 (1987).
J. L. Grem, et al., Cancer Treat Rep 71:1179–1184 (1987).
F. Gueritte-Voegelein, et al., Acta Crystallogr C46:781–784 (1990).
F. Gueritte-Voegelein, et al., J Med Chem 34:992–998 (1991).
W. Lorenz, et al., Agents Actions 7:63–67 (1977).
I. Ojima, et al., J Med Chem 37:1408–1410 (1994).
E. K. Rowinsky, et al., J Natl Cancer Inst 82:1247–1259 (1990).
A. Sharma and R. M. Straubinger, Pharm Res 11:889–896 (1994).
A. Sharma, et al., Cancer Res 53:5877–5881 (1993).
A. Sharma, et al., J Pharm Sci 84:1400–1404 (1995).
A. Sharma, et al., Cancer Lett 107:265–272 (1996).
U. S. Sharma, et al., J Pharm Sci 84:1223–1230 (1995).
R. M. Straubinger, In (M. Suffness ed.) *Taxol Science and Applications,* CRC Press, Boca Raton, pp. 237–258 (1995).

R. M. Straubinger, et al., J Natl Cancer Inst Monographs 15:69–78 (1993).

R. M. Straubinger, et al., In (G. Georg, et al., ed.) *Taxane anticancer agents: basic science and current status*, ACS Symposium Series, Washington, D.C., pp. 111–123 (1994).

M. Suffness, Ann Rep Med Chem 28:305–314 (1993).

E. Tomiak, et al., Annals Oncol 3:48 (1992).

D. G. Vander Velde, et al., J Am Chem Soc 115:11650–11651 (1993).

M. C. Wani, et al., J Am Chem Soc 93:2325–2327 (1971).

S. H. Yalkowsky and S. C. Valvani, Drug Intell and Clin Pharmacy 11:417–419 (1977).

What is claimed is:

1. A method of stabilizing a taxane in a dispersed system, which method comprises exposing the taxane to a molecule which improves physical stability of the taxane in the dispersed system.

2. The method of claim 2 wherein the molecule which improves physical stability of the taxane in the dispersed system improves solubility of the taxane in the dispersed system.

3. The method of claim 1 wherein exposing the taxane to a molecule comprises forming a taxane-containing dispersed system, and exposing the taxane-containing dispersed system to the molecule.

4. The method of claim 1 wherein exposing the taxane to a molecule comprises exposing the taxane to the molecule, and forming a taxane-containing dispersed system.

5. The method of claim 1 wherein the taxane is selected from the group consisting of paclitaxel, 7-epitaxol, 7-acetyl taxol, 10-desacetyl-taxol, 10-desacetyl-7-epitaxol, 7-xylosyltaxol, 10-desacetyl-7-glutaryltaxol, 7-N,N-dimethylglycyltaxol, 7-L-alanyltaxol, taxotere, docetaxel, SB-T-1011, and mixtures thereof.

6. The method of claim 1 wherein the dispersed system is selected from the group consisting of a liposome, a micelle, and an emulsion.

7. The method of claim 1 wherein the molecule decreases aggregation of the taxane.

8. The method of claim 1 wherein the molecule decreases stacking of the taxane.

9. The method of claim 1 wherein the molecule decreases dimerization of the taxane.

10. The method of claim 1 wherein the molecule is glycerol.

11. The method of claim 1 wherein the molecule is an alcohol.

12. The method of claim 11 wherein the alcohol is selected from the group consisting of propylene glycol, polyethylene glycol, and ethanol.

13. The method of claim 1 wherein the molecule is dimethyl sulfoxide.

14. The method of claim 1 wherein the molecule is $CH_3$.

15. The method of claim 1 wherein the molecule is acetic acid or acetic anhydride.

16. The method of claim 1 wherein the dispersed system is a liposome and the molecule is glycerol.

17. The method of claim 16 wherein the taxane is paclitaxel.

18. A stabilized taxane-containing dispersed system produced by the method of claim 1.

19. A stable taxane-containing liposome preparation comprising a liposome containing one or more taxanes present in the liposome in an amount of less than 20 mol % total taxane to liposome, wherein the liposome is suspended in a glycerol:water composition having at least 30% glycerol.

20. The stabilized taxane-containing liposome preparation of claim 19 wherein the taxane is selected from the group consisting of paclitaxel, 7-epitaxol, 7-acetyl taxol, 10-desacetyl-taxol, 10-desacetyl-7-epitaxol, 7-xylosyltaxol, 10-desacetyl-7-glutaryltaxol, 7-N,N-dimethylglycyltaxol, 7-L-alanyltaxol, taxotere, docetaxel, SB-T-1011, and mixtures thereof.

* * * * *

UNITED STATES PATENT AND TRADEMARK OFFICE
CERTIFICATE OF CORRECTION

PATENT NO.    : 6,348,215 B1
DATED         : February 19, 2002
INVENTOR(S)   : Robert M. Straubinger and Sathyamangalam V. Balasubramanian It is certified that error appears in the above-identified patent and that said Letters Patent is hereby corrected as shown below:

<u>Column 1,</u>
Line 6, insert the following pararaph:

-- The present invention was made with the support of the National Institute of Health Contract No. CA55251. The Federal Government may have the rights in this invention. --

Signed and Sealed this

Thirtieth Day of September, 2003

JAMES E. ROGAN
*Director of the United States Patent and Trademark Office*